United States Patent [19]

Mandroian

[11] 4,265,600

[45] May 5, 1981

[54] PUMP APPARATUS

[76] Inventor: Harold Mandroian, 2137 Los Amigos, La Canada, Calif. 91011

[21] Appl. No.: 939,924

[22] Filed: Sep. 5, 1978

[51] Int. Cl.³ .................................................. F04B 43/06
[52] U.S. Cl. ..................................... 417/379; 417/297; 417/384; 417/395; 92/97
[58] Field of Search ............... 417/297, 384, 389, 379, 417/395; 92/97

[56] References Cited

U.S. PATENT DOCUMENTS

| | | | |
|---|---|---|---|
| 2,289,617 | 7/1942 | Wood | 417/384 |
| 2,576,282 | 11/1951 | Chambers | 417/379 |
| 2,957,422 | 10/1960 | Loeber | 417/297 X |
| 3,036,525 | 5/1962 | Schulze et al. | 92/97 X |
| 3,045,874 | 7/1962 | Kogan et al. | 417/395 |
| 3,064,631 | 11/1962 | Schwander | 417/395 X |
| 3,101,058 | 8/1963 | Carr, Jr. et al. | 417/395 X |
| 3,232,524 | 2/1966 | Rice et al. | 417/395 X |
| 3,387,566 | 6/1968 | Temple | 417/568 X |
| 3,762,838 | 10/1973 | Sato | 417/395 |
| 3,947,156 | 3/1976 | Becker | 417/413 X |

FOREIGN PATENT DOCUMENTS 1256070 12/1971 United Kingdom ..................... 417/395

Primary Examiner—Leonard E. Smith

Attorney, Agent, or Firm—Nilsson, Robbins, Dalgarn, Berliner, Carson & Wurst

[57] ABSTRACT

A pump for transferring precise amounts of fluid from a container to a patient. A pump apparatus has a defined volume pump chamber divided by a diaphragm into a pumping fluid portion and a pumped fluid portion. The pumped fluid portion receives and exhausts pumped fluid in response to a decrease or increase in pressure in the pumping fluid portion of the pump chamber. The diaphragm and the defined volume pumping chamber provide accurate per cycle pumping volumes. The pumping fluid pressure is varied by periodically electrically heating a ribbon filament in a pumping fluid chamber thereby increasing the temperature and therefore the pressure and/or volume of the pumping fluid. The pumped fluid enters the pumping chamber through a one-way valve as the pumped fluid portion volume expands and is exhausted through a second one-way valve as the volume of the pumped fluid portion contracts. Control circuitry is provided to allow variations in the pulse repetition rate and pulsewidth. A feedback control loop may also be provided by sensing, for example, the fluid flow rate, pressure, temperature or other dependent variable and generating an error signal therefrom.

1 Claim, 6 Drawing Figures

PUMP APPARATUS

BACKGROUND OF THE INVENTION

The present invention relates to pumps and, in particular, to pumps having accurate pumping rates and pumping volumes.

Fluid pumps are typically based upon the use of a rotating or reciprocating device such as an impeller which is bearing mounted and driven by some motive means such as an electric motor. Such mechanical pumps, while reasonably efficient, uniformly suffer from the problems of wear of the moving parts as well as significant levels of audible noise. In order to solve the problems of wear, a pump having essentially no moving parts was developed and is disclosed in my U.S. Pat. No. 3,898,017, issued Aug. 5, 1975. In that patent, the heater ribbon is placed in the chamber containing the pumped fluid. This allows the fluid being pumped to come in contact with the heating ribbon. Such direct contact may not be desirable in some medical applications where it is desired to pump fluids having a delicate or fragile structure or which are subject to breakdown in the presence of high temperature. In addition, it is frequently necessary to keep the pumped fluid separated from a reusable heater to maintain a sterile environment for the pumped fluid. Such was not possible in the prior patent.

The present invention in meeting these problems provides a pump which incorporates a movable diaphragm for separating the fluid being pumped from the heating ribbon or element so that the pumped fluid is not affected by the heat from the heating element, and further will not be contaminated by contaminants which may exist around the heating element or in the chamber in which the heating element is placed. The pumping of the pumped fluid thus occurs in response to the expansion and contraction of a pumping fluid which is different from the pumped fluid and which preferably has a high expansion ratio and low specific heat. Although such a pumping fluid is preferably a gas, it may be a liquid or may be a fluid which changes state, for example, from a liquid to a gas upon heating and then back to a liquid when the heater is cool. In addition, the present invention in using a diaphragm in a pumping chamber with a fixed volume provides a means of very accurately defining the pumped volume of the fluid. This occurs by causing the diaphragm to be displaced by the pumping fluid upon its expansion against the sides of the pumping chamber thereby expelling all of the pumped fluid in the chamber. Thus, the volume of the fluid pumped on each cycle of the pump is accurately defined by the volume of the pumping chamber. The present invention also provides a means for easily adjusting the flow rate, as well as providing increased fluid pressures. The pump of the present invention may be a positive displacement type pump or may incorporate a variable displacement feature by controlling the amount by which the pumping fluid expands due to heating by the heater. Finally, the present pump invention is free of audible noise.

In U.S. Pat. No. 2,884,866 issued May 5, 1959, a pumping mechanism is disclosed which attempted to provide accurate pumping volumes. However, in that patent, no fixed volume chamber was provided to define an accurate per cycle pumped volume. Finally, the interior of the sock-type flexible member defining the cycle pumping volume could not be accurately evacuated on each cycle thus resulting in additional inaccuracy in pumping volume and rate. It will be appreciated that in many I.V. pumping applications, pumping accuracy unachievable by the above-cited patent but easily obtained by the present invention, is a necessity.

Various other apparatus using pistons (which have undesirable friction and sealing characteristics), manual or independent valve operation, single-cycle rather than continuous multiple-cycle operation, inter-mingling of the pumped and the pumping fluid, no volume-defining pumping chamber, and various other disadvantages are described in various of the U.S. Pat. Nos. 2,389,067; 2,576,282; 2,867,224; 2,884,866; 3,045,874; 3,074,596; 3,099,222; 3,149,754; 3,604,821; 3,645,649; 3,859,012; 3,901,629; and Re. 27,740.

SUMMARY OF THE INVENTION

The present invention comprises a pumping system having a pump apparatus coupled between a reservoir and a destination for pumping fluid from the reservoir along a flow path in which a pumping chamber is placed. A diaphragm bifurcates the pumping chamber into a liquid portion and a gas portion. A heater apparatus is coupled to the pump apparatus and comprises a heating chamber for containing a quantity of gas. The heating chamber is coupled by a passageway to the gas portion of the pumping chamber. An electrical heater is also provided in the pumping chamber for heating the quantity of gas. Finally, a heater control means is coupled to the electrical heater and provides intermittent electrical pulses for energizing the heater and thereby heating the gas to cause the gas to expand which, in turn, causes the diaphragm to expand forcing the fluid from the fluid portion of the pumping chamber.

Additional features of the present invention may be provided and include one or more potentiometers or other control devices known in the art which may be incorporated in the heater control circuitry to allow the pulse repetition rate or the pulse duration of the electrical pulses energizing the electrical heater or both to be varied.

Also in the preferred embodiment, two one-way valves are utilized, one in the input passageway and a second in the exit passageway to assure that the fluid is not pumped back toward the reservoir from which it came.

It will also be appreciated that the pump may be of either the positive-displacement or the variable-displacement type. In one embodiment of the invention, a feedback control loop may be provided by incorporating, for example, a flow rate sensor in the hydraulic circuit of the pump. The sensor generates a signal proportional to the flow rate which may be fed back and utilized to vary the amplitude, period, or duration of the electrical pulse provided to the heater to thereby vary the amount of heating and, thus, expansion of the pumping fluid in the pumping fluid chamber. Such a feedback control loop is particularly useful in a variable displacement pumping embodiment.

Another embodiment of the present invention provides a means of unloading an exit valve means so that pumped fluid under a nominal head pressure will flow through the pump without the action of the diaphragm to thereby allow air to be easily bled from the pump. A load on the exit valve may subsequently be replaced, with fluid flow thereafter occurring only under the action of diaphragm movement in response to increased and decreased pressure of the pumping fluid.

Yet another embodiment of the present invention provides a means for increasing the fluid pressure in the exit passageway by providing a first, large surface area diaphragm which expands and contracts in response to increased and decreased pumping fluid pressure. A member with a decreased surface area is then coupled to the first diaphragm. This decreased surface area is positioned against a second diaphragm with the equivalent force. Thus, since the second diaphragm has a smaller surface area and the same total amount of force is applied, the force in units of pounds per square inch is thereby increased resulting in increased fluid pressure in the exit passageway.

Of course, it will be appreciated that many other variations and modifications of the present invention and its various components are possible such as replacing the valves in the input and exit passageways with an egress restriction means or ingress restriction means to induce flow in a single direction by providing less resistance to flow in one direction than in the other. Such a modification is disclosed in my patent No. 3,898,017. Also it will be appreciated that the fluid utilized in the pumping fluid chamber may be air or a gas such as argon or helium which have greater thermal expansion per unit of heat energy than air.

BRIEF DESCRIPTION OF THE DRAWINGS

The invention will be better understood from the detailed description below taken in conjunction with the drawings wherein like reference characters refer to like parts throughout and in which.

DETAILED DESCRIPTION OF THE PREFERRED EMBODIMENTS

Figure 1:
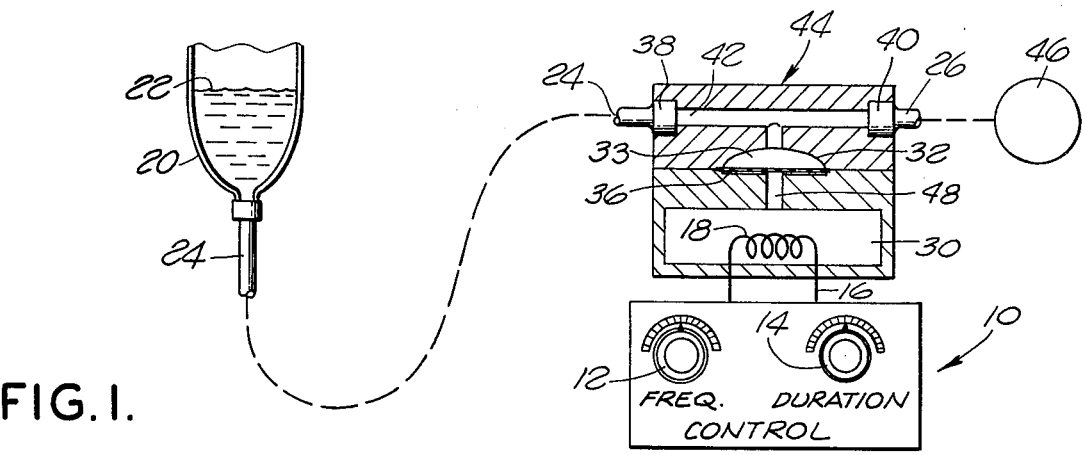
FIG. 1 is a simplified representation showing a cross-section of a pump apparatus and the associated control unit for varying the frequency and pulsewidth of the signal applied to the heater.

The pump system of the present invention may be generally understood by reference to FIG. 1 which shows a pump apparatus 44 electrically coupled to a control means 10 for pumping fluid 22 from a container 20 to a destination 46. In the preferred application of the various embodiments of the present invention, the pump introduces a fluid or drug from a pouch or other container into the blood stream of a patient who would typically be the destination for the fluid.

More specifically, the pump apparatus 44 generally has an enclosed chamber 30 which contains a pumping fluid which may be air or some other gas, which is connected by a port or passageway to a pumping chamber 32. The pumping chamber 32 is bifurcated by a membrane or diaphragm 36 which moves back and forth within the chamber 32 in response to increases and decreases in the gas pressure in the chamber 30.

Fluid is introduced into the pump from the reservoir 20 along an input passageway 24. A one-way valve 38 is interposed between the passageway 24 and an internal passageway 42 to assure that the fluid 22 will not be pumped back into the input passageway 24. Connected between the internal passageway 42 and an exit passageway 26 is a second one-way valve 40 which prevents fluid expelled from the pump apparatus 44 from returning to the internal passageway 42.

In operation, once all of the air has been bled from the input passageway 24, a fluid portion 33 of the pumping chamber 32, and the internal passageway 42, an increase in gas (or fluid) pressure in the chamber 30 causes the diaphragm 36 to be displaced in the direction of the fluid portion 33 of the pumping chamber 32 thereby decreasing the volume of the fluid portion 33 forcing fluid out into the internal passageway 42. Because the valve 38 prevents the fluid from flowing back into the input passageway 24, the displaced fluid is forced from the internal passageway 40 through the valve 40 into the exit passageway 26.

When the gas pressure in the chamber 30 again decreases, for example when the heater is deenergized, the diaphragm 36 contracts toward the chamber 30 causing a volume increase in the fluid portion 33 causing fluid to enter through the valve 38, the internal passageway 42, and into the fluid portion 33. No fluid enters through the valve 40 because the pressure causes the valve 40 to close.

Although various methods may be utilized to increase and decrease the gas pressure in the chamber 30 to achieve the pumping action required, the preferred method is to intermittently or periodically heat the gas in the chamber 30 by periodically applying an electrical current through a ribbon heater 18 which is connected by the leads 16 to the control unit 10. The periodic pulses of electricity through the heater ribbon 18 cause the expansion and contraction of the gas in the chamber 30 necessary to periodically displace the diaphragm 36. Numerous circuits are available which provide periodic power pulses and may, for example, be a power circuit such as that described in my U.S. Pat. No. 3,898,017, issued Aug. 5, 1975, or may be one of the various circuit arrangements disclosed in literature provided by National Semiconductor Corporation in conjunction with their ML-555 timer/pulse generator.

In one embodiment, the circuit described in U.S. Pat. No. 3,898,017 may be modified by providing a potentiometer whose adjustment can change the pulse repetition rate provided to the heating ribbon 18. In such an embodiment, the control unit 10 is provided with a frequency control knob 12 coupled to the potentiometer whereby the frequency of the pulses may be varied. The control unit may also incorporate a second variable resistor connected to a control knob 14 for controlling the duration of each pulse. Such modifications in circuits to provide periodic pulses whereby the pulse rate and the pulse width may be controlled by inputs provided to electrically control an oscillator circuit such as that described in accordance with the circuits shown in various brochures illustrating applications of the No. 555 timer available, for example, from National Semiconductor Corporation. More specifically, both frequency and pulse width can be controlled by applying a voltage to the proper pins on the 555 timer.

Figure 2:
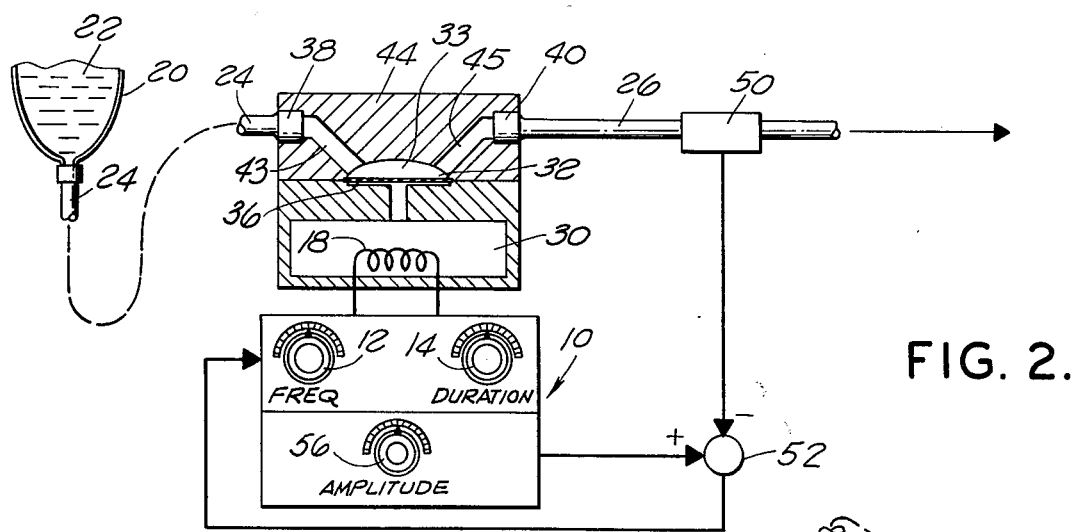
FIG. 2 is a simplified representation of a second embodiment of the present invention showing a separate input port and exit port and incorporating a feedback control loop for varying the amplitude, pulse width, or frequency of the electrical signal to the heater.

Referring to FIG. 2, the present invention is shown incorporating a feedback control loop for controlling the rate at which fluid flows through the exit passageway 26. Such a system is particularly applicable when the pump apparatus 44 is of a variable displacement type where the diaphragm 36 expands only partly into the pumped fluid portion. Thus, by controlling the amount of heating in the chamber 30, and thus the amount of increased pressure pushing against the diaphragm 36, a very precise pumping volume can be achieved for each cycle of pumping. Further, since the amount of heat energy supplied by the heating ribbon 18 to the chamber 30 is related to the amount of power flowing through the heating ribbon 18 supplied by the control unit 10, it can be seen that a voltage amplitude setting provided by a third knob 56 which controls a third potentiometer, pulse width control, or frequency control may be utilized to precisely set the volume and, thus, the flow rate of fluid through the pump. Of course, any other control mechanism to control the pulse width and frequency may be utilized.

In order to implement such a representative control system, a flow rate sensor 50 may be provided in the exit passageway 26 to sense the rate of flow or the pressure or any other relevant parameter indicative of the pumping volume, rate, or pressure and generate a substantially constant voltage output proportional to that flow rate pressure or volume sensed. This voltage value is subtracted from a voltage value which is set by the amplitude potentiometer controlled by the knob 56 at a summing junction 52 to provide an error signal output. Of course, it will be appreciated that the sensor 50 and the voltage output from the amplitude potentiometer will be calibrated so that when the flow rate sensed by the sensor 50 equals the values set by the knob 56, then the error will be zero and, thus, the error signal from the summing junction 52 will be zero.

The error signal from the summing junction 52 is then utilized by the pulse rate and duration control circuitry controlled by the frequency control 12 and the duration control 14 to thereby provide feedback control for the amplitude or duration of the pulses utilized to heat the heating ribbon 18. Of course, various other techniques and control configurations may be used for automatically sensing and controlling the amount of energy utilized to heat the gas in the chamber 30. For example, a direct feedback control for the pulse repetition rate or pulse duration without the need of an additional amplitude potentiometer may be incorporated.

Referring particularly to the pump portion of FIG. 2 as compared to the pump portion of FIG. 1, it will be seen that in FIG. 2 an input passageway 43 and an output passageway 45, each with separate ports to the pumping chamber, may be provided rather than the single port of FIG. 1, without departing from the spirit of the present invention.

Figure 3:
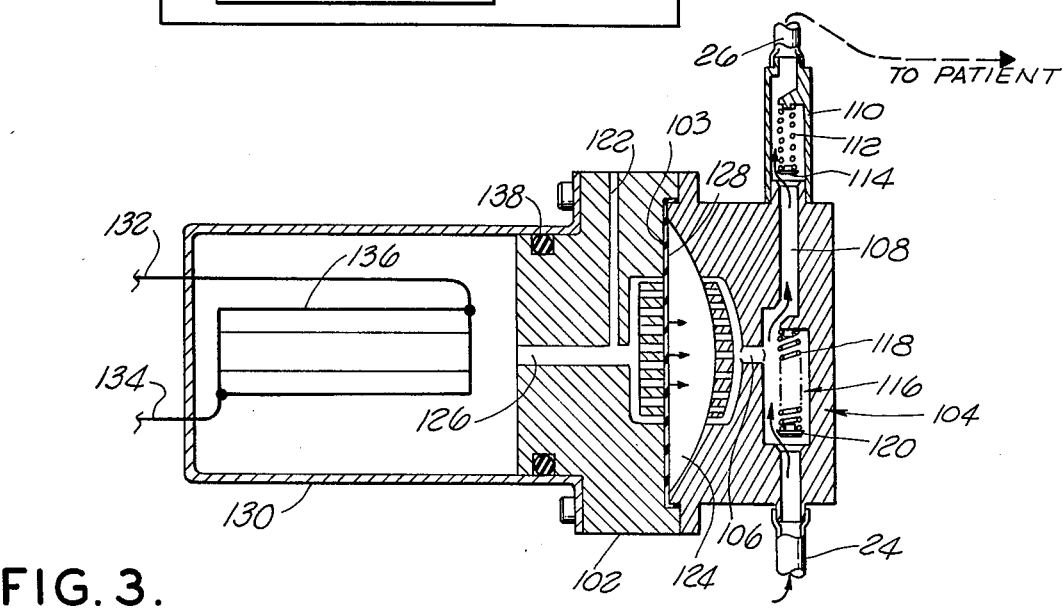
FIG. 3 is a detailed cross-sectional view of one embodiment of a pump apparatus which may be utilized in conjunction with the present invention.

Referring now to FIG. 3, a detailed cross-sectional view of one embodiment of the pump apparatus of the present invention is illustrated whereby fluid enters through an input passageway 24 and exits through an exit passageway 26. Between the input passageway 24 and the exit passageway 26 is an input valve 116 comprising a spring 118 fixed at one end to one wall of a pump casing 104 and connected at its other end to a valve poppet 120. When fluid is caused to enter an internal passageway 108 of the pump member 104, fluid pressure causes the valve poppet 120 to open against the spring 118 allowing fluid to flow around the valve poppet 120 and into the internal passageway 108.

In a similar fashion, an exit valve 110 is provided with a spring 112 and a valve poppet 114 which opens when pressure provided by the movement of a diaphragm 128 forces fluid out from a pumping chamber 124.

The pumping chamber 124 is coupled by a passageway 106 to the internal passageway 108 to define a continuous internal volume of the pumping member 104. The pumping chamber 124 may be defined by a concave impression in one surface of the member 104 with a diaphragm 128 placed across the mouth of the concavity. The diaphragm 128 and the member 104 are then inserted into a circular, recessed region with a substantially planar surface 103 in a second member 102 so that the member 104 and the member 102 fit tightly together with the diaphragm 128 therebetween to provide a substantially airtight joint between the member 102 and the member 104. The diaphragm thus separates the fluid on one side of the diaphragm from the gas or other pumping fluid having a periodically increased pressure on the other side. Of course, it will be appreciated that the planar surface 103 may be concave such as the planar surface 171 shown in FIG. 5, particularly when the pumped fluid has a positive bead pressure.

In practice, it is preferable that the pumping chamber 124 be defined by a generally concave surface against which the membrane 128 presses when the gas pressure in the chamber 120 is high and a substantially flat surface opposite to the concave surface against which the member 128 returns when the gas pressure in the chamber 130 is relatively low. In addition, while the passageway 106 may have a single orifice or port in the pumping chamber 124, it is preferable that smaller, multiple orifices be provided in order to maintain the accuracy of the volume since the diaphragm will extend into a larger orifice and thereby cause a larger volume to be displaced. Such an increased displacement can result in a significant and unacceptable error when accurate pumping volumes and desired. Of course, other methods may be utilized to prevent the diaphragm from protruding into the orifice by which the pumping chamber is connected to the internal passageway 108. For example, referring momentarily to FIG. 4, porous surfaces 158 and 159, such as a fine screen or other similar surface, may be placed on the surfaces of a pumping chamber 150 to cover the orifices from the input port and the exit port 160 and 162 respectively and the input air port 164. The porous surface thus allows the fluid to flow through but prevents the membrane from distorting into either the input, the exit, or the air input ports. An alternative method of preventing such distortion is shown in FIG. 3 where the pumped fluid port and pumping fluid ports are multiple, smaller cross-sectional area ports.

Returning to FIG. 3, an air passageway 126 connects the pumping chamber on the gas chamber side of the membrane 128 to a gas chamber 130. Another passageway 122 may also be provided having a very small cross-sectional area to allow the pressure inside the chamber 130 to be equalized with the outside pressures over a relatively long period of time. Such a small passageway is preferable to prevent distortions in the membrane 128 caused by unequal pressures which, in turn, may cause pumping errors. It will be appreciated, of course, that the time required for the pressure inside the chamber 130 to be equalized with the pressure outside the chamber 130 through the passageway 122 must be greater than the pulse width of the electrical signal applied through the electrical leads 132 and 134 to the heating ribbon apparatus 136. If this were not the case, then the increased pressure produced by heating the gas in the chamber 130 would be dissipated through the passageway 122 rather than causing the diaphragm 128 to expand into the fluid portion of the pumping chamber 124. The gas chamber 130 may be made a part of the member 102 or may be a separate member which is firmly attached to the member 102 with the connection made airtight by a seal 138.

Figure 4:
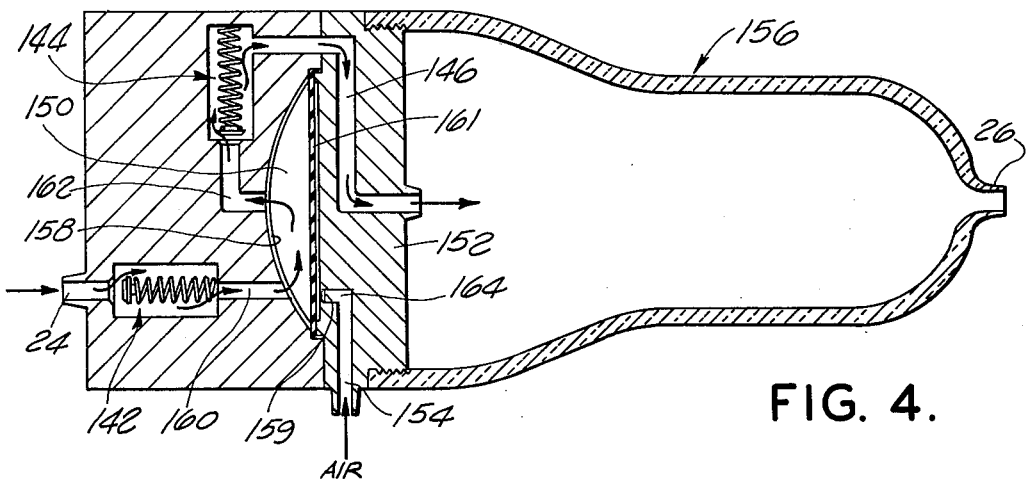
FIG. 4 is another embodiment of a pump apparatus in which the pumping chamber has a separate input port and exit port.

Referring to FIG. 4, an alternative embodiment incorporating the principles of the present invention is shown having an input passageway 24 leading into an input valve 142 which is coupled by a passageway to a port 160 in a pumping chamber 150. An exit port 162 is provided approximately in the center of the concave surface of the pumping chamber 150 which leads to an exit valve 144. Heading from the exit valve is an exit passageway 146 which empties fluid into a drip chamber 156. A gas passageway 154 has an orifice 164 in the flat surface of the pumping chamber 150 which is provided by the member 152. A diaphragm 161 bifurcates the pump chamber 150 between the concave surface with the input and exit ports 160 and 162 and the flat surface with the port 164. As previously described, a porous surface or member 158 may be placed to cover the input port 160 and exit port 162. Of course, a similar membrane 159 may be placed over the gas port 154.

In operation, the embodiment illustrated in FIG. 4 causes fluid to first enter through the first input valve 142 into the pumping chamber 150. The fluid is then expelled through the exit port 162 and the exit valve 144 into the exit passageway 146 and the drip chamber 156. Thus, in the embodiment of FIG. 4, fluid is actually pumped through the fluid portion of the pump chamber 150 utilizing an input and an exit port, while in the prior embodiment illustrated in FIGS. 1 and 3, fluid entered and was expelled through the same port. As previously discussed, the valves are preferably one-way valves, although there may be egress and ingress restriction means which induce flow in one direction without completely preventing fluid from flowing in a direction opposite to the desired direction of flow. Such an arrangement is disclosed in my U.S. Pat. No. 3,898,017. The embodiment of FIG. 4 illustrates that numerous arrangements of the various passageways and valves are possible without departing from the teaching of the present invention.

Figure 5:
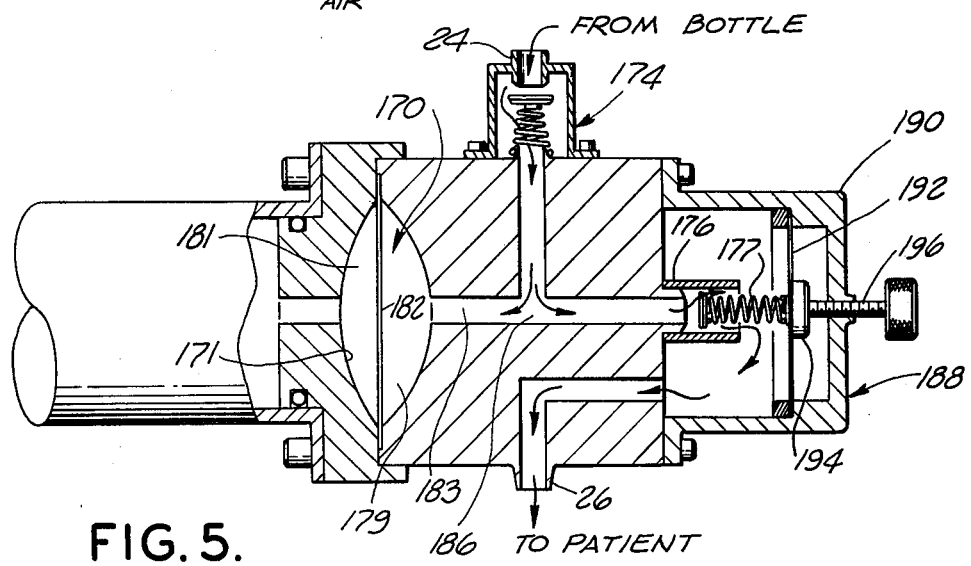
FIG. 5 is a detailed cross-sectional view of a pump apparatus which provides a means for unloading the exit valve.

Referring now to FIG. 5, another embodiment of the present invention is illustrated having a pump chamber 170 bifurcated by a diaphragm 182 into a gas portion 181 and a fluid portion 179. The pumping chamber 170 is coupled by a connecting passageway 183 to a passageway 186 between an input valve 174 and an exit valve 176. The volume of the connecting passageway 183 and the pumping chamber 170 define a pump chamber volume while the volume defined by the passageway 186 defines a passageway volume. In operation, it is preferable that the pumping chamber volume be greater than the passageway volume to insure passage of entrapped air from the system when the pump is operating.

In the embodiment shown in FIG. 5, the exit valve 176 may be either loaded or unloaded to facilitate bleeding air from the system. Thus, the spring 177, which is a part of the exit valve 176, is attached to a second membrane or diaphragm 192 so that the valve 176 is in the unloaded condition when the diaphragm 192 is not displaced. When in the unloaded condition, the valve 176 permits a relatively small value of fluid pressure in the input passageway 24 to open the valve 176 thus allowing fluid to enter through the valve 174 and exit through the valve 176 without requiring pumping action by the diaphragm 182. In order to load the valve 176, a support member 190 may be provided with a screw or lever apparatus 196 which has a pressing member 194 positioned adjacent to the diaphragm 192. Thus, by appropriately positioning the screw or lever apparatus 196, the pressing member 194 moves inward relative to the support member 190 causing the diaphragm 192 to depress thereby loading the valve poppet 176 by compressing spring 177. Thereafter, the valve 176 opens only in response to pumping action provided by the diaphragm 182. Of course, other means for loading the valve may be incorporated without departing from the spirit of the present invention.

Figure 6:
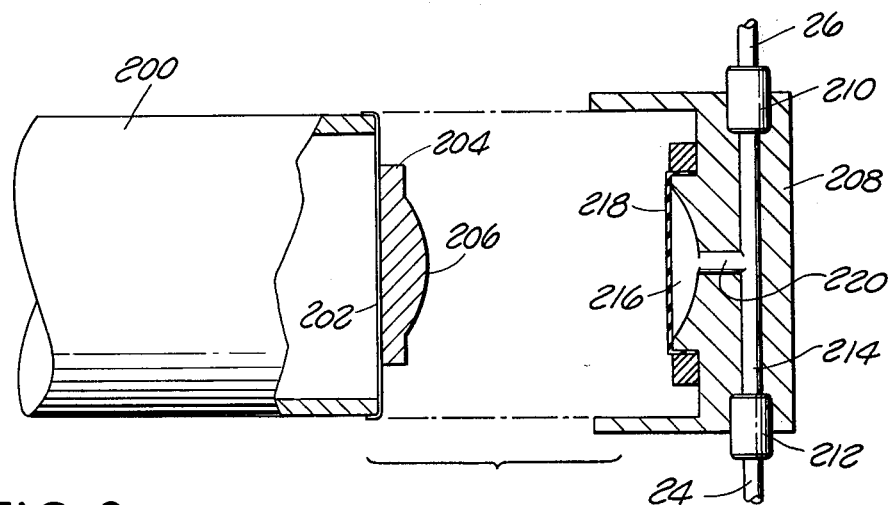
FIG. 6 is a detailed cross-sectional representation of a pump apparatus which may be utilized to increase the pressure of the pumped fluid to a higher level than that provided directly by the gas in the heater chamber.

In FIG. 6, there is illustrated a means by which the pumping pressure in the exit passageway 126 may be increased utilizing hydraulic principles. Thus, a gas chamber 200 is provided with a first diaphrgam 202 placed across one of its ends whereby the increased gas pressure due to heating the gas is applied across the total surface area of the diaphragm 202. Adjacent to the diaphragm 202 on the side opposite the gas chamber 200, a member 204 may be placed having a convex region 206 on a surface opposite to that placed against the diaphragm 202. A pump member 208 is then provided having an input passageway valve 212 and an exit passageway valve 210 connected by an internal passageway 214. A concave region is provided in the member 208 which is connected by a coupling passageway 220 to the internal passageway 214. A diaphragm 218 is placed across the mouth of the concave portion of the pump member 208 to thereby define an enclosed pumping chamber 216.

In operation, the pumping member 208 is placed adjacent to the member 204 which is adjacent to the diaphragm 202. The convex portion 206 of the member 204 is positioned opposite to the concave portion of the member 208. It is preferable that the convex portion 206 be substantially the reciprocal of the concave portion in the member 208. The member 204 is initially positioned to be immediately next to and possibly touching the diaphragm 218 when the gas in the chamber 200 is cool. When the gas is heated, causing the pressure to increase in the chamber 200, the diaphragm 202 expands causing the member 204 to push against the diaphragm 218 causing the fluid in the chamber 216 to be pushed out into the passageway 214 and out through the exit passageway 26. When the gas in the chamber 200 is cooled, the member 204 returns to its quiescent position and the diaphragm 218 returns to its initial position causing fluid to again enter the pumping chamber 216 through the input valve 212.

As taught by the principles of hydraulics, the pressure in the chamber 200 is applied against the total surface area of the diaphragm 202 causing the member 204 to push outwardly with a given force. The entire force is concentrated by the convex portion 206 and is applied to the much smaller surface area of the diaphragm 218. Thus, the force per unit area is increased which results in an increase in the pressure with which the fluid is pumped through the pump member 208. The above embodiment is particularly useful since it has been discovered that there is a practical upper limit on the pressure which may be provided against a surface utilizing the heated gas technique herein disclosed.

It will be appreciated, of course, that the pumping member 208 may be placed next to the diaphragm 202 and, thus, be removable therewith and the member 204 fixed to a stationary location opposite the pumping member 208.

The present invention, thus, provides a very accurate apparatus for pumping small quantities of fluid from a reservoir to a destination and is particularly applicable in intravenous applications where the rate and quantity of fluids introduced into a patient are critical.

What is claimed is:

1. A pumping system comprising:
   pumping apparatus coupled for pumping fluid from a reservoir to a destination along a flow path comprising a passageway means, a volume defining pumping chamber in the passageway means, the pumping chamber having a predetermined volume, and a diaphragm means for defining at least a pumped fluid portion of the pumping chamber, the diaphragm means comprising:
      a first diaphragm having a first surface area against which the variable gas pressure is applied; and
      a pressure increasing means which comprises a first member having a member surface with a raised region whose cross-sectional area in the plane of the member is smaller than the first surface area, the raised region having a shape substantially the reciprocal of the shape of the pumping chamber surface in the pumped fluid portion, and a second diaphragm positioned for defining an enclosed volume comprising the pumped fluid portion of the pumping chamber, the second diaphragm positioned adjacent to the raised region for being depressed by the raised region to decrease the volume of the pumped fluid portion of the pump chamber in response to an increase in the pressure of the pumping fluid;
   heater apparatus comprising a quantity of pumping fluid, a heating chamber for containing said quantity of pumping fluid, the heating chamber coupled for applying a force to the diaphragm to decrease the volume of the pumped fluid portion of the pumping chamber when the pressure of the quantity of pumping fluid increases, and a heater in the heating chamber for heating the quantity of pumping fluid and thereby increasing the pressure and volume of the quantity of pumping fluid; and
   heater control means for providing electrical pulses for intermittently energizing the heater.

* * * * *